(12) United States Patent
Noel

(10) Patent No.: US 6,497,116 B2
(45) Date of Patent: Dec. 24, 2002

(54) APPARATUS FOR ABSTRACTING HEAT WITH A SOLID--LIQUID MATRIX UTILIZING A KINETIC--CIRCULATION-- KINETIC HEAT TRANSFER CYCLE

(76) Inventor: Thomas P. Noel, 6519 N. 86th St., Scottsdale, AZ (US) 85250

( * ) Notice: Subject to any disclaimer, the term of this patent is extended or adjusted under 35 U.S.C. 154(b) by 0 days.

(21) Appl. No.: 09/776,486

(22) Filed: Feb. 2, 2001

(65) Prior Publication Data

US 2002/0148249 A1 Oct. 17, 2002

(51) Int. Cl.[7] .................................................. F25D 3/08
(52) U.S. Cl. ........................................... 62/530; 62/457.2
(58) Field of Search ....................... 62/530, 529, 457.2, 62/457.9, 371

(56) References Cited

U.S. PATENT DOCUMENTS 2,595,328 A * 5/1952 Bowen .............................. 62/1
5,069,208 A * 12/1991 Noppel et al. ............... 128/403
5,840,080 A * 11/1998 Der Ovanesian ............ 607/114
6,074,415 A * 6/2000 Der Ovanesian ............ 607/114

* cited by examiner

Primary Examiner—Denise L. Esquivel
Assistant Examiner—Melvin Jones
(74) Attorney, Agent, or Firm—Tod R. Nissle, P.C.

(57) ABSTRACT

Apparatus for abstracting heat comprises a container charged with a first liquid and with small auxiliary containers free to circulate in the first liquid. Each of the small auxiliary containers is charged with a second liquid. The freezing point of the first liquid is less than the second liquid such that when the second liquid is frozen, the first liquid is not, is free to circulate, and permits the auxiliary containers to circulate in the first liquid.

2 Claims, 1 Drawing Sheet

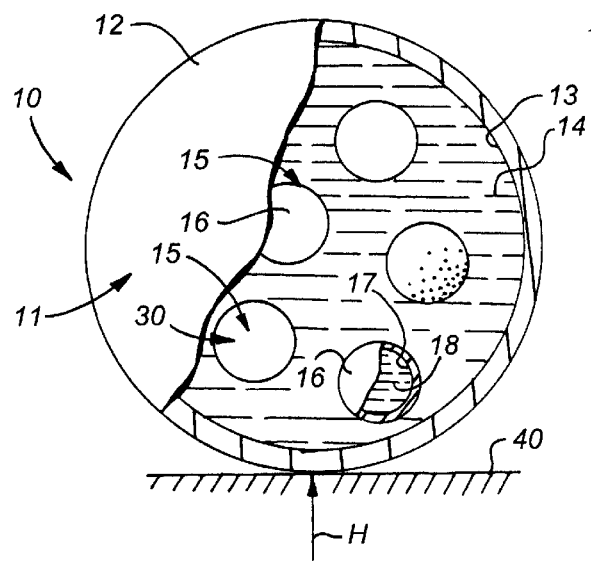
FIG. 1
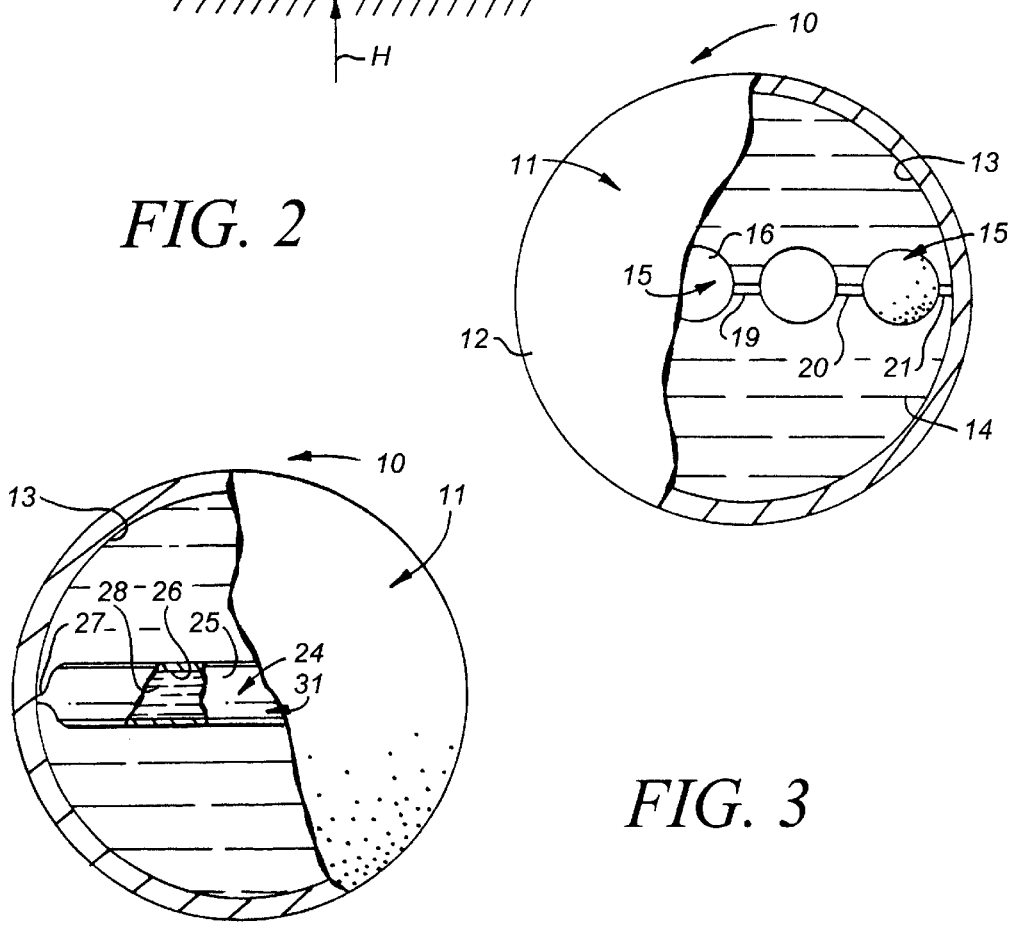
FIG. 2
FIG. 3

APPARATUS FOR ABSTRACTING HEAT WITH A SOLID--LIQUID MATRIX UTILIZING A KINETIC--CIRCULATION--KINETIC HEAT TRANSFER CYCLE

This invention pertains to apparatus for abstracting heat from a substance.

More particularly, the invention pertains to an improved apparatus which utilizes a matrix comprised of liquids and solids to abstract, over an extended period of time, heat from a substance.

So called "cold packs" are well known and typically, for example, comprise pliable, hollow, vinyl containers filled with a gelatin. In use, the cold pack is frozen and is placed against an individual's neck or other part of the individual's body to cool the individual. One such conventional cold pack is marketed under the trademark "THERAPAC" and comprises a twelve inch-by-twelve inch two ply vinyl container filled with a white odorless insoluble gelatin. Another conventional cold pack is marketed under the trademark "COLPAC" and comprises a twelve inch-by-twelve inch single ply polymer container filled with a gray odorless soluble gelatin. Such conventional cold packs are widely disseminated and effectively absorb heat. One principal disadvantage of such cold packs is that they have a relatively short-lived ability to stay cold. For example, when the THERAPAC and COLPAC cold packs noted above are removed from a freezer, the temperature on the outer surface of the cold pack can be five degrees F. After about an hour, the temperature can be about forty-five to fifty degrees F. After about two hours, the temperature on the outer surface of the cold packs can be about fifty-two to fifty-eight degrees F. After about three hours, the temperature can be about sixty-five to seventy degrees F. Consequently, after only an hour the temperature of the outer surface of each of the cold packs is well above freezing.

Accordingly, it would be highly desirable to provide an improved cold pack which would, after being exposed to ambient temperature, maintain a low temperature for an extended period of time.

Therefore, it is a principal object of the invention to provide an improved apparatus for abstracting heat from a solid, liquid, gas or other substance.

A further object of the instant invention is to provide an improved cold pack which will maintain a cold temperature for an extended period of time after being exposed to a temperature greater than that of the cold pack.

These and other, further and more specific objects and advantages of the invention will be apparent to those skilled in the art from the following detailed description thereof, taken in conjunction with the drawings, in which:

FIG. 1 is an elevation view illustrating a heat transfer device constructed in accordance with the principles of the invention;

FIG. 2 is an elevation view illustrating an alternate embodiment of the invention; and, FIG. 3 is an elevation view illustrating yet another embodiment of the invention.

Briefly, in accordance with the invention, I provide an improved heat transfer device for use in contacting and drawing heat away from a substance. The heat transfer device includes a hollow primary container including a wall, and a first liquid housed in the container; and, includes at least one hollow auxiliary container in the first liquid and including a wall, and a second liquid housed in the auxiliary container. The second liquid has a freezing point less than the freezing point of the first liquid.

In another embodiment of the invention, I provide an improved method for cooling a substance. The method includes the steps of providing a heat transfer device. The heat transfer device includes a hollow primary container including a wall, and a first liquid housed in the container. The primary container also includes at least one hollow auxiliary container in the first liquid. The auxiliary container includes a wall, and a second liquid housed in the auxiliary container. The second liquid has a freezing point less than the freezing point of the first liquid. The method also includes the steps of cooling the heat transfer device to freeze the second liquid; and, contacting the substance with the heat transfer device.

In a further embodiment of the invention, I provide an improved method for cooling a substance. The method includes the step of providing a heat transfer device. The heat transfer device includes a hollow primary container. The primary container includes a wall, and a first liquid housed in the container. The primary container also includes at least one hollow auxiliary container in the first liquid. The hollow auxiliary container includes a wall, and a second liquid housed in the wall of the auxiliary container. The second liquid has a freezing point less than the freezing point of the first liquid. The method also includes the steps of cooling the heat transfer device to freeze the second liquid; and, contacting the substance with the heat transfer device such that heat is abstracted from the substance into the first liquid by conduction through the wall of the primary container, such that heat abstracted into the first liquid by conduction through the wall of the primary container causes the liquid to have a nonuniform temperature and produces circulatory motion in the liquid due to ariation in the density of the liquid and the action of gravity, and such that heat is abstracted from the first liquid by the conduction through the wall of the auxiliary container.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a heat transfer device generally identified by reference character 10. Device 10 includes a spherical hollow primary container having a wall 11 including spherical outer surface 12 and spherical inner surface 13. A liquid 14 is housed inside the primary container. At least one auxiliary spherical hollow container 15 is in and free to move and circulate about the reservoir formed by liquid 14. Each hollow container 15 includes a spherical wall 30 having a spherical outer surface 16 and a spherical inner surface 17. A liquid 18 is housed inside each auxiliary container 15. Liquid 14 has a lower (cooler) freezing point than liquid 18, and preferably, but not necessarily, has a freezing point lower than the coldest temperatures found in conventional household or commercial freezers. By way of example, and not limitation, liquid 14 presently comprises propylene glycol and liquid 18 comprises water. Liquid 18 preferably has a freezing point greater or equal to the coldest temperature found in conventional household or commercial freezers.

Other examples of compositions that can be utilized as liquid 14 or liquid 18 include aqueous solutions of ethyl alcohol, methyl alcohol, PRESTONE, iso-propyl alcohol, and glycerol. Magnesium chloride, sodium chloride, and calcium chloride brines can be utilized. Refrigerants which can be utilized as liquid 14 include ammonia, ethyl chloride, and methyl chloride.

The wall 11 is preferably, although not necessarily, fabricated from a pliable vinyl or other pliable material so that wall 11 will conform to a part of an individual's body or will conform to some other object that is contacted by heat transfer device 10. Similarly, the wall 30 is preferably, although not necessarily, fabricated from a pliable vinyl or other pliable material so that wall 30 will conform to a part of an individual's body or will conform to some other object. As would be appreciated by those of skill in the art, device 10 and walls 11 and 15 need not be spherical and can be made to have any desired shape, contour, and dimension. Walls 11 and 15 need not be pliable and can be substantially rigid.

In use of the heat transfer device 10, device 10 is placed in a freezer. Liquid 18, being water, freezes. Liquid 14, being propylene glycol, does not freeze. After liquid 18 freezes, device 10 is removed from the freezer and placed against a portion 40 of an individual's body or against some other object or substance so that device 10 absorbs heat H. Heat is absorbed through wall 11 and into liquid 14 by the transfer of kinetic energy from particle to particle. When heat is absorbed by liquid 14, liquid 14 has a non-uniform temperature, i.e., liquid near wall 11 is warmer and has a greater enthalpy than liquid farther away from wall 11. If liquid near wall 11 has a different temperature, the density of the liquid near wall 11 is different than the density of cooler liquid farther away from wall 11. This density differential, along with the force of gravity, causes circulation and movement of liquid 14. When, during this circulation and movement, warmed liquid 14 passes by and contacts an auxiliary spherical hollow container 15, heat is absorbed through wall 30 and into frozen liquid 18 by the transfer of kinetic energy from particle to particle.

The heat transfer device of FIG. 2 is identical to that of FIG. 1 except that auxiliary containers 15 are connected in a chain to each other and to the inner surface of wall 13 by links 19, 20, and 21, respectively. This chain can be slack so that containers 15 can, to a degree, move about in liquid 14, or, the chain can be substantially rigid so it maintains its shape and dimension even if pliable wall 11 is displaced.

The heat transfer device of FIG. 3 is identical to that of FIG. 1 except that auxiliary containers 15 are removed and replaced by an elongate hollow auxiliary container 31 having a cylindrical wall 24 with a cylindrical outer surface 25 and a cylindrical inner surface 26. Container 31 is filled with a liquid 28 which, like liquid 18, has a freezing point which is greater (warmer) than that of liquid 14.

The use of the devices of FIGS. 2 and 3 is comparable to that of the heat transfer device of FIG. 1. In FIG. 2, auxiliary containers 15 absorb heat from liquid 14. In FIG. 3, auxiliary container 31 absorbs heat from liquid 14.

The ratio of the mass of liquid 14 with respect to the mass of liquid 18 (or 28) in a device 10 can vary as desired, but is presently preferably about 1:1. As the mass of liquid 18 with respect to the mass of liquid 14 increases, the heat absorbing capacity of liquid 18 increases, but there is less of liquid 14 to circulate to containers 15 heat which is absorbed from wall 11. It is believed that if the mass of liquid 18 greatly exceeds that of liquid 14 (e.g., the ratio of liquid 18 to liquid 14 is, for example, 8:1 ), then heat will tend to be absorbed directly by containers 15 instead of first being absorbed by liquid 14 and transferred to containers 15. This would defeat a primary feature of the invention. The use of liquid 14 to circulate heat to containers 15 is believed central to the invention and is believed, at least in part, responsible for why the heat transfer apparatus of the invention stays cool for unusually long periods of time. The ratio of liquid 18 to liquid 14 is preferably, but not necessarily, in the range of 3:1 to 1:3, most preferably in the range of 2:1 to 1:2.

The materials utilized to construct walls 11 and 30 and 24 affect the rate of heat transfer. Thicker walls normally transfer heat at a slower rate; thinner wall at a faster rate. While polymer material is desirable in walls 11, 24, 30 because pliable polymer materials are readily available, incorporating metal or other materials which facilitate the transfer of heat is also desirable.

When a device 10 is placed in a freezer to solidify liquid 18, liquid 14 can have a composition which permits it to turn to a gel, but preferably does not solidify. It is preferred that liquid 14 remain a liquid or become a gel so that device 10 remains pliable after being frozen. Similarly, when liquid 18 is frozen, it may turn to a gel and may not completely solidify.

The following example is given by way of demonstration and not limitation of the scope of the invention.

EXAMPLE

The following were obtained:

1. A twelve inch long by twelve inch wide "THERAPAC" (TM) two ply vinyl "cold pack" containing a white odorless insoluble gelatin. This cold pack was identified as "A".

2. A twelve inch long by twelve inch wide "COLPAC" (TM) single ply plastic "cold pack" filled with a gray odorless soluble gelatin. This cold pack was identified as "B".

3. A cold pack was constructed in accordance with the invention and comprised a ten inch long by ten inch wide two ply plastic container filled with one and three-fourths pounds of propylene glycol and a plurality of small elastic liquid-filled rubber containers each having a diameter in the range of one inch to one and one-quarter inches. The liquid in each of the small rubber containers was water. One and three-fourths pounds of water was used to fill the small rubber containers, i.e., each small rubber container contained significantly less than one and three-fourths pounds of water, and, if all the water in all of the small rubber containers were poured in a container, the water would have weighed one and three-fourth pounds. The rubber containers could move about freely in the propylene glycol. Each ply in the plastic bag had a thickness of about two to three mils. The wall thickness of each rubber container was about two to three mils. This cold pack was identified as "C".

Cold packs A, B, C were all placed at the same time in a freezer. After several hours, cold packs A, B, C were removed at the same time from the freezer and placed on a flat table top in a room. The room temperature was eighty degrees and was maintained at eighty degrees while the following measurements were made. Measurements were made when the cold packs were removed from the freezer and at hourly intervals thereafter up to four hours. Each time measurements were taken, a measurement was taken on the outer surface of each cold pack and on the interior of each cold pack. The results are summarized below in Tables I and II.

TABLE I

Surface Temperature Measurements of Cold Packs A, B, C

| Cold Pack | Temperature Measurements (Degrees F.) | | | | |
|---|---|---|---|---|---|
| | At removal | 1 hour | 2 hours | 3 hours | 4 hours |
| A | 5 | 48 | 56 | 72 | 77 |
| B | 5 | 47 | 55 | 73 | 80 |
| C | 10 | 39 | 39 | 40 | 42 |

TABLE II

Interior Temperature Measurements of Cold Packs A, B, C

| Cold Pack | Temperature Measurements (Degrees F.) | | | | |
|---|---|---|---|---|---|
| | At removal | 1 hour | 2 hours | 3 hours | 4 hours |
| A | 0 | 47 | 55 | 65 | 75 |
| B | 0 | 49 | 57 | 65 | 75 |
| C | 15 | 15 | 32 | 34 | 36 |

The above results demonstrate that the cold pack of the invention (identified as "C") remained much colder for much longer than the conventional cold packs identified as "A" and "B". These results were surprising and unexpected and are believed to demonstrate the utility and novelty of the heat transfer device of the invention.

Having described my invention in such terms as to enable those of skill in the art to make and practice it, and having described the presently preferred embodiments thereof,

I claim:

1. A method for cooling a substance, including the steps of
   (a) providing a heat transfer device including
      (i) a hollow primary container including
         a wall, and
         a first liquid housed in said container; and,
      (ii) at least one hollow auxiliary container in said first liquid and including
         a wall, and
         a second liquid housed in said auxiliary container;
         said second liquid having a freezing point less than the freezing point of said first liquid;
   (b) cooling said heat transfer device to freeze said second liquid;
   (c) contacting the substance with the heat transfer device such that heat
      (i) is abstracted from the substance into said first liquid by conduction through said wall of said primary container,
      (ii) abstracted into said first liquid by conduction through said wall of said primary container causes said liquid to have a nonuniform temperature and produces circulatory motion in said liquid due to variation in the density of said liquid and the action of gravity,
      (iii) is abstracted from said first liquid by said conduction through said wall of said auxiliary container.

2. A method for cooling a substance, including the steps of
   (a) providing a heat transfer device including
      (i) a hollow primary container including
         a wall, and
         a first liquid housed in said container; and,
      (ii) at least one hollow auxiliary container in said first liquid and including
         a wall, and
         a second liquid housed in said auxiliary container;
         said second liquid having a freezing point less than the freezing point of said first liquid;
   (b) cooling said heat transfer device to freeze said second liquid;
   (c) contacting the substance with the heat transfer device.

* * * * *